US00PP12180P2

(12) United States Plant Patent
Lemon

(10) Patent No.: US PP12,180 P2
(45) Date of Patent: Oct. 30, 2001

(54) GERANIUM PLANT NAMED 'WHITE TRUFFLES'

(75) Inventor: David Lemon, Lompoc, CA (US)

(73) Assignee: John Bodger and Sons Company, South El Monte, CA (US)

( * ) Notice: Subject to any disclaimer, the term of this patent is extended or adjusted under 35 U.S.C. 154(b) by 0 days.

(21) Appl. No.: 09/119,912

(22) Filed: Jul. 21, 1998

(51) Int. Cl.[7] ..... A01H 5/00
(52) U.S. Cl. ..... Plt./326
(58) Field of Search ..... Plt./326

(56) References Cited

U.S. PATENT DOCUMENTS

P.P. 3,173 * 5/1972 Knicely et al. ..... Plt./326
P.P. 10,012 * 11/1997 Lemon ..... Plt./326

* cited by examiner

*Primary Examiner*—Bruce R. Campell
*Assistant Examiner*—Wendy A Baker
(74) *Attorney, Agent, or Firm*—Fulwider Patton Lee & Utecht, LLP

(57) ABSTRACT

The cultivar is characterized by the bright clear white flower color over a very dark green foliage. Its superior performance even in adverse weather conditions is typified by its quick rooting time, enhanced cutting production and large plant size. The cultivar is distinguished by its large semi-double floret which resists shattering.

1 Drawing Sheet

BACKGROUND OF THE NEW PLANT

The present invention comprises a new and distinct cultivar of *Pelargonium×hortorum* known by the varietal name, 'White Truffles' (Oglevee No. 3252, Bodger No. 3 GM 35-3). The new variety was discovered in a selective breeding program by David Lemon at Bodger Seeds, Ltd., Lompoc, Calif. The new variety is a selection from the crossing of 'Showcase White' (U.S. Plant Pat. No. 8,284) with 'La Paloma' (unpatented).

The new cultivar was first asexually reproduced by cuttings at Oglevee Ltd., located at 152 Oglevee Lane, Connellsville, Pa., 15425 and has been repeatedly asexually reproduced by cuttings at Oglevee Ltd. in Connellsville, Pa. It has been found to retain its distinctive characteristics through successive propagations.

The new cultivar was grown in a glass greenhouse in Connellsville, Pa., using full light, 60° Fahrenheit night temperature, 68° Fahrenheit day temperature, and grown in a soilless media using a constant fertilizer of 200–250 parts per million of Nitrogen and Potassium, in full light. The claimed plant was grown from a rooted cutting, potted in a 10 cm pot and exhibited a six week response time from the rooted cutting to a flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted in a 20 cm pot on approximately Jan. 15, 1996 and flowering on approximately Feb. 27, 1996, under full light in the greenhouse, and color readings were taken in the Oglevee office under 200–220 foot candles of cool white fluorescent light using The Royal Horticultural Society of London Colour Chart.

THE PLANT

Classification:
- *Botanical.*—*Pelargonium×hortorum.*
- *Commercial.*—Florist's Geranium 'White Truffles' (Florist's geraniums are high quality plants which grow well outdoors).

Form: Medium mound habit.
- *Height.*—21 cm from the surface of the media to the top of the flower clusters; 19.0–21.0 cm above foliage.
- *Growth.*—Free basal branching.
- *Strength.*—Needs no artificial support.

Foliage: Slightly reflective; Dark green with no prominent zone although not prominent there is a slight zone in the leaves; Leaves slightly upturned; Stalked leaf attachment.

Leaves:
- *Size.*—9.0–11.0 cm across when fully expanded.
- *Shape.*—Reniform; cordate base.
- *Margin.*—Crenate.
- *Texture.*—Slightly pubescent.
- *Color.*—Top: Green Group 137A. Bottom: Green Group 137C. Zone: slight color change in zone area; zone not obvious.
- *Ribs and veins.*—Palmate venation. Color: Green Group 143C.

Petioles:
- *Length.*—6.5–7.5 cm.
- *Color.*—Green Group 143C.

Stem:
*Color.*—Green Group 143C.
*Internode length.*—3.4–4.0 cm.

THE BUD (UMBEL)

This information refers to the stage of development when the peduncle has fully elongated and buds are just showing color.

Shape: Elliptical; cluster. This information refers to the entire bud cluster. "Elliptical" refers to the shape of individual buds within the cluster. Number of buds per cluster is 25–30.

Size: 4.0 cm across as florets are just cracking color creamy pale yellow to yellow green before open Yellow Group 4D umbel depth 3.0 cm as florets are just showing color.

INFLORESCENCE

Blooming habit: Continuous; free and early flowering; observed number of florets 25–30 per umbel.

Borne: Floret on pedicel; pedicel on peduncle; 5.0–8.0 cm above foliage.

Closed florets: Bud Size: 1.0–1.5 cm long.

Size: Fully Open Bloom: 8.5–9.5 cm across.

Open florets:
*Form.*—Open to flat and slightly cupped; semi-double.
*Color.*—Top: White Group 155D. Bottom: On florets that are just open color is Yellow Group 4D, fading as petal ages. Outer edge is White Group 155D; center of petal is White Group 155A. Eye: None.
*Petals.*—8–10 in number.
*Size.*—1.7–2.5 cm across.
*Texture and appearance.*—Dark leaved, bright clear white large floret presentation; young florets having slightly yellow appearance on underside of petal.

Petaloids:
*Quantity.*—6–8 petaloids.
*Shape.*—Irregular; twisted and tubular.
*Color.*—*Top: White Group* 155D. Bottom: White Group 155D.

Pedicel:
*Length.*—2.3–2.7 cm.
*Color.*—Green Group 143C.

Peduncle:
*Length.*—15.0–17.0 cm long.
*Color.*—Green Group 143C.

Persistence:
*Disease resistance.*—No known special disease resistence compared with other Geraniums.
*Lasting quality.*—Less petal shattering and browning than most other currently available cultivars.

REPRODUCTIVE ORGANS

Stamens:
*Anthers.*—Length: 2.0–3.0 mm.
*Filaments.*—Length: 7.0–9.0 mm. Color: White.
*Pollen.*—Young pollen: Red Group 38C. Mature pollen: Orange-Red Group 34B.

Pistils:
*Number.*—1.
*Length.*—9.0–10.0 mm.
*Stigma.*—Color: pale yellow green; 5–6 parted.
*Style.*—Length: 5.0–6.0 mm.

Ovaries:
*Color.*—Green; superior pubescent.
*Length.*—4.0–5.0 mm.

Fruit: None.

GENERAL CHARACTERISTICS

'White Truffles' brings a crisp clean white bloom flower above a very dark green foliage and is a great improvement over 'Showcase White'. 'Whites Truffles' has an improved plant size and cutting production as well as an enhanced rooting time and outdoor performance.

I claim:

1. A new and distinct variety of Gerranium plant, substantially as shown and described.

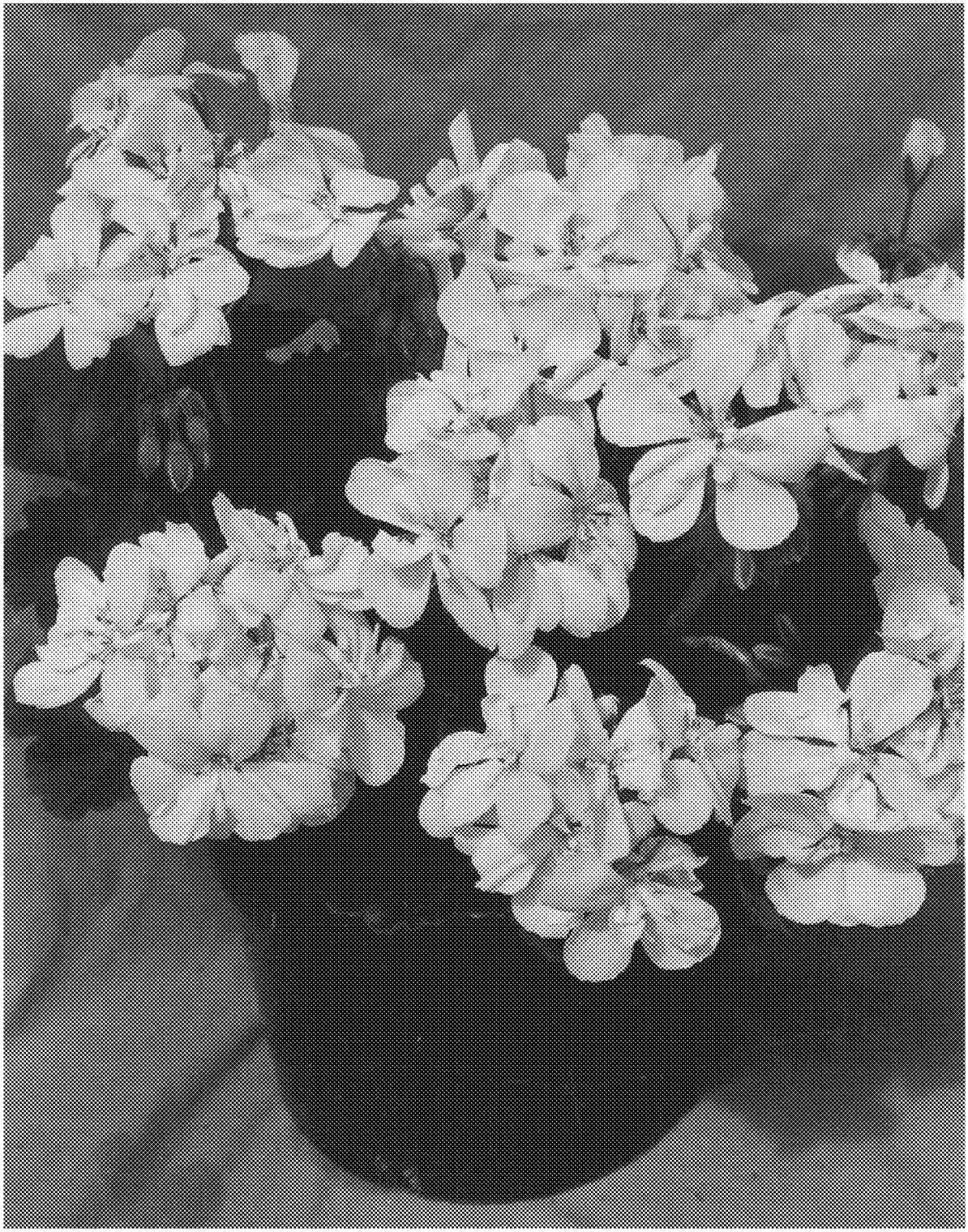

* * * * *